(12) United States Patent
Peist et al.

(10) Patent No.: US 8,377,638 B2
(45) Date of Patent: Feb. 19, 2013

(54) PROCESS FOR THE DETECTION OF CYTOSINE METHYLATIONS

(75) Inventors: Ralf Peist, Hilden (DE); Thorsten Träger, Haan (DE); Roland Fabis, Leverkusen (DE); Axel Deeg, Wuppertal (DE)

(73) Assignee: Qiagen GmbH, Hilden (DE)

( * ) Notice: Subject to any disclaimer, the term of this patent is extended or adjusted under 35 U.S.C. 154(b) by 586 days.

(21) Appl. No.: 12/159,838

(22) PCT Filed: Jan. 8, 2007

(86) PCT No.: PCT/EP2007/050152
§ 371 (c)(1),
(2), (4) Date: Feb. 24, 2010

(87) PCT Pub. No.: WO2007/077262
PCT Pub. Date: Jul. 12, 2007

(65) Prior Publication Data
US 2010/0297614 A1  Nov. 25, 2010

(30) Foreign Application Priority Data
Jan. 6, 2006 (DE) .......... 10 2006 001 161

(51) Int. Cl.
*C12Q 1/68* (2006.01)
*C07H 21/00* (2006.01)
*C07H 21/02* (2006.01)
*C07H 21/04* (2006.01)

(52) U.S. Cl. ....... 435/6.1; 536/22.1; 536/23.1; 536/24.3
(58) Field of Classification Search .......... 435/6.1, 435/6.11, 6.12, 91.2; 536/23.1, 24.3
See application file for complete search history.

(56) References Cited

U.S. PATENT DOCUMENTS
6,960,436 B2 * 11/2005 Cottrell ............... 435/6.12
2004/0152080 A1 * 8/2004 Berlin .................... 435/6

FOREIGN PATENT DOCUMENTS
WO  WO 00/70090  11/2000
WO  WO 01/98528  12/2001

OTHER PUBLICATIONS

EpiTect Bisulfite Handbook (Apr. 2006).*
Senol et al., Fluid Phase Equilibria 106 : 169 (1995).*
International Search Report No. PCT/EP2007/050152, dated Apr. 16, 2007, 6 pgs.

* cited by examiner

*Primary Examiner* — Ethan C Whisenant
(74) *Attorney, Agent, or Firm* — Baker Donelson Bearman Caldwell & Berkowitz, PC

(57) ABSTRACT

The invention concerns a method for the detection of cytosine methylations in DNA and a kit for undertaking an assay according to the method of the invention.

20 Claims, No Drawings

US 8,377,638 B2

PROCESS FOR THE DETECTION OF CYTOSINE METHYLATIONS

CROSS REFERENCE TO RELATED APPLICATIONS

This application is a §371 National Stage Application of PCT/EP2007/050152, filed Jan. 8, 2007, which claims priority to German Application 10 2006 001 161.9, filed Jan. 6, 2006, the content of which is incorporated by reference.

FIELD OF THE INVENTION

Background of the Invention

The present invention concerns a method for the detection of cytosine methylations in DNA.

As a result of the methodological developments in molecular biology of recent years, well studied planes of observation have been the genes themselves, the translation of these genes into RNA, and the resulting proteins. When during the course of the development of an individual which gene is switched on, and how activation and inhibition of specific genes in certain cells and tissues are controlled can be correlated to the extent and character of the methylation of the genes or the genome. In this respect pathogenic states express themselves in a modified methylation pattern of individual genes or the genome.

5-Methylcytosine is the most frequently covalently modified base in the DNA of eukaryotic cells. For example, it plays a role in the regulation of transcription, in genetic imprinting and in tumour genesis. The identification of 5-methylcytosine as component of genetic information is therefore of considerable interest. 5-Methylcytosine positions cannot be identified by sequencing, however, since 5-methylcytosine has the same base pair behaviour as cytosine. Moreover, the epigenetic information which 5-methylcytosines carry is totally lost during PCR amplification.

A relatively new and meanwhile most frequently used method in the investigation of DNA for 5-methylcytosine is based on the specific reaction of bisulphite with cytosine, which after subsequent alkaline hydrolysis is converted into uracil, which corresponds to thymidine in its base pair behaviour. In contrast, 5-methylcytosine is not modified under these conditions. Thus the original DNA is modified in such a way that methylcytosine, which originally cannot be distinguished from cytosine in its hybridisation behaviour, can now be detected by "standard" molecular biology techniques as the only remaining cytosine, for example by amplification and hybridisation or sequencing. All these techniques are based on base pairing, which is now fully exploited. The state of the art in respect of sensitivity is defined by a method which incorporates the DNA under investigation in an agarose matrix in a way that inhibits diffusion and renaturation of DNA (bisulphite reacts only on single-strand DNA) and replaces all precipitation and purification steps by rapid dialysis (Olek, A. et al., Nucl. Acids Res. 1996, 24, 5064-5066). Individual cells can be investigated with this method, which demonstrates the potential of this method. However, hitherto only individual regions of up to about 3000 base pair length have been investigated, a global investigation of cells for thousands of possible methylation analyses is not possible. However, this method too cannot reliably analyse very small fragments from small amounts of sample. In spite of protection against diffusion, they are lost through the matrix.

With few exceptions (e.g. B. Zechnigk, M. et al., Eur. J. Hum. Gen. 1997, 5, 94-98), the bisulphite technique has hitherto only been used in research. Always short, specific fragments of a known gene are amplified after bisulphite treatment and either completely sequenced (Olek, A. and Walter, J., Nat. Genet. 1997, 17, 275-276) or individual cytosine positions identified in a "primer extension reaction" (Gonzalgo, M. L. and Jones, P. A., Nucl. Acids Res. 1997, 25, 2529-2531, WO-95/00669-A1) or an enzyme digestion (Xiong, Z. and Laird, P. W., Nucl. Acid Res. 1997, 25, 2532-2534). Detection by hybridisation has also been described (Olek et al., WO-99/28498-A2).

Fluorescence-labelled probes are frequently used for the probing of an immobilised DNA array. The simple attachment of Cy3 and Cy5 dyes to the 5'-OH of the respective probe is particularly suitable for fluorescent labelling. The detection of the fluorescence of the hybridised probe is carried out, for example, with a confocal microscope. In addition many others, the dyes Cy3 and Cy5 are available commercially.

The polymerase chain reaction (or PCR) method is a method used in gene technology with which it is possible to multiply in vitro a small number of molecules of a desired DNA sequence by a factor of $10^6$ to $10^8$ in a short time. Normally two synthetic oligodeoxynucleotide primers with a length of ca. 15 to 30 nucleotide are needed, the sequences of which are complementary to the start and end sequences of the sister strand of the DNA to be multiplied ("amplified"), together with a mixture of 4-deoxynucleotide-5-triphosphates and a thermostable DNA polymerase that can tolerate at least a brief heating to 95° C. without impairment of function.

For many applications it is necessary in a PCR to determine the number of DNA molecules originally present. There are therefore different approaches which allow the number of DNA copies formed to be calculated even during individual steps of the chain reaction and hence to arrive at this value. Usually the middle, so-called exponential phase of the PCR is chosen in which the number of DNA templates actually almost doubles during each cycle.

Matrix-assisted laser desorption/ionisation mass spectrometry (MALDI-TOF) is a highly effective development for the analysis of biomolecules. (Karas, M. and Hillenkamp, F. (1988), Laser desorption ionisation of proteins with molecular masses exceeding 10,000 daltons. Anal. Chem. 60:2299-2301). An analyte is embedded in a light-absorbing matrix. The matrix is evaporated by a short laser pulse and the analyte molecule is transmitted unfragmented into the gas phase. Ionisation of the analyte is achieved by collision with matrix molecules. An applied potential accelerates the ions into a field-free flight tube. The ions are accelerated differently based on their masses. Smaller ions reach the detector earlier than larger. MALDI-TOF spectroscopy is ideally suited for the analysis of peptides and proteins.

The analysis of nucleic acids is somewhat more difficult, (Gut, I. G. and Beck, S. 1 (1995)), DNA and Matrix Assisted Laser Desorption Ionization Mass Spectrometry. Molecular Biology: Current Innovations and Future Trends 1: 147-157). Sensitivity is about 100 times poorer for nucleic acids than for peptides, and decreases overproportionally with increasing fragment size. The ionisation process by the matrix is significantly less efficient for nucleic acids that have a multiply negatively charge backbone.

The choice of matrix plays an pivotally important role in MALDI-TOF spectroscopy. A number of very efficient matrices have been found for the desorption of peptides that provide a very fine crystallisation. There are indeed a number of suitable matrices for DNA, but the difference in sensitivity has not been reduced as a consequence. The difference in sensitivity can be reduced by modifying the DNA chemically in such a way that they become more like a peptide. Phosphorothioate nucleic acids, in which the usual phosphate of the backbone is substituted by thiophosphate, may be converted into a charge-neutral DNA by simple alkylation chemistry (Gut, I. G. and Beck, S. (1995), A procedure for selective DNA alkylation and detection by mass spectrometry. Nucleic Acids Res. 23: 1367-1373). The coupling of a "charge tag" to this modified DNA results in an increase in sensitivity by the same amount as found for peptides. The increased stability of the analysis towards impurities that greatly complicate the detection of unmodified substrates is a further advantage of "charge-tagging".

Genomic DNA is obtained from DNA of cell, tissue or other experimental samples by standard methods. This standard methodology is found in references such as Fritsch and Maniatis eds., Molecular Cloning: A Laboratory Manual, 1989.

Urea improves the efficiency of bisulphite treatment prior to the sequencing of 5-methylcytosine in genomic DNA (Paulin R, Grigg G W, Davey M W, Piper A A. (1998), Nucleic Acids Res. 26:5009-5010).

The problem of the present invention is to provide an improved method for the detection of cytosine methylations in DNA which overcomes the disadvantages of the prior art.

SUMMARY OF THE INVENTION

The problem is solved in that a method for the detection of cytosine methylations is provided wherein the following procedures carried out:

a) a genomic DNA sample is incubated with a solution of a bisulphite (=hydrogen sulphite, disulphite) within a concentration range between 0.1 and 6 mol/l, wherein tetrahydrofurfuryl alcohol is present;

b) the reaction mixture obtained is subjected either to a purification or depletion step so that the reactants added in step a) are removed or the treated DNA sample is diluted with water or an aqueous solution so that the reagents added in step a) do not interfere with the following reactions;

e) detection is carried out as to what extent the sequence has changed by the treatment according to step a) in comparison to the genomic DNA sample and a conclusion is made on the methylation status of at least one locus in the genomic DNA sample.

DETAILED DESCRIPTION OF A PREFERRED EMBODIMENT

The problem can also be solved in that a method for the detection of cytosine methylations in DNA is provided wherein the following procedures are carried out:

a) a genomic DNA sample is incubated with a solution of a bisulphite (=hydrogen sulphite, disulphite) within a concentration range between 0.1 and 6 mol/l, wherein in addition to at least one radical scavenger and tetrahydrofurfuryl alcohol optionally further denaturing reagent(s) and/or solvents are present;

b) the reaction mixture obtained is subjected either to a purification or depletion step so that the reactants added in step a) are removed or the treated DNA sample is diluted with water or an aqueous solution so that the reagents added in step a) do not interfere with the following reactions;

c) the DNA sample is optionally subjected to a desulphonation step, either during the purification or depletion step, or the DNA sample is subjected to a desulphonation step in a subsequent reaction;

d) the DNA sample is optionally amplified in a polymerase reaction;

e) detection is carried out as to what extent the sequence has changed by the treatment according to step a) in comparison to the genomic DNA sample and a conclusion is made on the methylation status of at least one locus in the genomic DNA sample.

It was found surprisingly that compared to other detergents or solvents, in respect of environmental compatibility and toxicity tetrahydrofurfuryl alcohol is advantageous for use in the method according to the invention in comparison to other solvents used.

It is preferred thereby that the denaturing reagent and/or solvent is selected from the following list of compounds or compound classes: polyethylene glycol dialkyl ether, dioxan and substituted derivates, urea or derivates, acetonitrile, primary alcohols, secondary alcohols, tertiary alcohols, diethylene glycol dialkyl ether, triethylene glycol dialkyl ether, tetraethylene glycol dialkyl ether, pentaethylene glycol dialkyl ether, hexaethylene glycol dialkyl ether, DMSO, THF.

It is further preferred that the radical scavenger is selected from the following group of compounds:
di-, trihydroxybenzenes, green tea extract, pine bark extract (pycnogenol), *ginkgo biloba* extract (EGb 761), flavonoid mixture of different fruit and vegetable extracts (GNLD), Bio-Normalizer (Sun-O Corp), DPPH (1,1-diphenyl-2-picrylhydrazyl), NDGA (nordihydroguaiaretic acid), Trolox (6-hydroxy-2,5,7,8-tetramethylchroman-2-carboxylic acid), 2,6-di-tert-butylphenol, 4-methyl-di-tert-butylphenol, 4-methoxy-di-tert-butylphenol, 2,6-di-tert-butyl-p-cresol, 3,4-dihydroxybenzoic acid, vitamin C, vitamin E, vitamin Q, hydroquinone, ubiquinone, lignanes, hydroxyterpenes, flavonoids, curcumin, tannins, retinoic acid compounds, Ge-132 bisbetacarboxyethyl germanium sesquioxide, superoxide dismutase (SOD), superoxide catalase, alpha-naphthoflavone, *ginkgo biloba* extract (EGb 761), di(2-methyl-5-chlorophenyl)dithionate and Cu(II)-derivates, mebendazole, CS (chloroform soluble) alkaloidal extract, 4-(3,5-di-tert-butyl-4-hydroxyphenyl)-3-hydroxy-1,2-naphthoquinone, 4-(3,5-di-tert-butyl-4-hydroxyphenyl)- 3-methoxy-1,2-naphthoquinone, 4-(3,5-di-tert-butyl-4- hydroxyphenyl)-1,2-naphthoquinone, 2-(3,5-di-tert-butyl-4-hydroxyphenyl)-3-bromo-1,4-naphthoquinone, 2-(3,5-d i-tert-butyl-4-hydroxyphenyl)-3-chloro-1,4-naphthoquinone, 2-(3,5-di-tert-butyl-4-hydroxyphenyl)-3-methoxy-1,4-naphthoquinone, 2-(3,5-di-tert-butyl-4-hydroxyphenyl)-3-hydroxy-1,4-naphthoquinone, 2-(3,5-di-tert-butyl-4-hydroxyphenyl)-1,4- naphthoquinone, 4-(3,5-di-tert-butyl-4-hydroxyphenyl)-3-hydroxy-5,5,8,8-tetramethyl-5,6,7,8-tetrahydro-1,2- anthraquinone, 4-(3,5-di-tert-butyl-4-hydroxyphenyl)-3-methoxy-5,5,8,8-tetramethyl-5,6,7,8-tetrahydro-1,2- anthraquinone, 4-(3,5-di-tert-butyl-4-hydroxyphenyl)-5,5,8,8-tetramethyl-5,6,7,8-tetrahydro-1,2-anthraquinone, 3-bromo-4- (3,5-di-tert-butyl-4-hydroxyphenyl)- 5,5,8,8-tetramethyl-5,6,7,8-tetrahydro-1,2-anthraquinone, 2-(3,5-di-tert-butyl-4-oxocyclohexa-2,5-dienylidene)-indan-1,3-dione, 2-(3,5-di-tert-butyl-4-oxocyclohexa-2,5-dienylidene)-3,4-epoxy-3-hydroxy-4-methoxy-3,4-dihydro-2H- naphthalen-1-one, 2-(3,5-di-tert-butyl-4- oxocyclohexa-2,5-dienylidene)-3,4-epoxy-3,4-dimethoxy-3,4-dihydro-2H-naphthalen-1-one, 2-(3,5-di-tert-butyl-4- hydroxyphenyl)-indan-1-one, 3,3-di[2-(3,5-di-tert-butyl-4- hydroxyphenyl)-inden-1-one)-3-yl, 2-(3,5-di-tert-butyl-4- hydroxyphenyl)-3-bromo-5,5,8,8-tetramethyl-5,6,7,8-tetrahydro-1,4-anthraquinone, 2-(3,5-di-tert-butyl-4- hydroxyphenyl)-3-chloro-5,5,8,8-tetramethyl-5,6,7,8-tetrahydro-1,4-anthraquinone, 2-(3,5-di-tert-butyl-4-hydroxyphenyl)-3-methoxy-5,5,8,8-tetramethyl-5,6,7,8-tetrahydro-1,4-anthraquinone, 2-(3,5-di-tert-butyl-4-hydroxyphenyl)-3-hydroxy-5,5,8,8-tetramethyl-5,6,7,8-tetrahydro-1,4-anthraquinone, 2-(3,5-di-tert-butyl-4-hydroxyphenyl)-5,5,8,8-tetramethyl- 5,6,7,8-tetrahydro-1,4-anthraquinone, 2-bromo-3-(3-bromo-5-tert-butyl-4-hydroxyphenyl)- 5,5,8,8-tetramethyl-5,6,7,8-tetrahydro-1,4-anthraquinone, 2-bromo-3-(3,5-dibromo-4-hydroxyphenyl)-5,5,8,8-tetramethyl-5,6,7,8- tetrahydro-1,4-anthraquinone, 2-bromo-3-(3- bromo-5-tert-butyl-4-hydroxyphenyl)-3-hydroxy-5,5,8,8-tetramethyl-5,6,7,8-tetrahydro-1,4-anthraquinone, 3-bromo-2-(3,5-di-tert-butyl-4-hydroxyphenyl)-1,4-anthraquinone, 2-(3,5-di-tert-butyl-4-hydroxyphenyl)-3- methoxy-1,4-anthraquinone, 2-(3,5-di-tert-butyl-4-hydroxyphenyl)-3-hydroxy-1,4-anthraquinone, 5,5,8,8-tetramethyl-5,6,7,8-tetrahydronaphthalen-1,3-diol, 3-methoxy-5,5,8,8-tetramethyl-5,6,7,8-tetrahydronaphthalen-1-ol, 4-(3-chloro-5,5,8,8-tetramethyl-1,4-dioxo-1,4,5,6,7,8-hexahydroanthracen-2-yl)benzoic acid, methyl-4-(3-chloro-5,5,8,8-tetramethyl-1,4-dioxo-1,4,5,6,7,8-hexahydroanthracen-2-yl)benzoate, 4-(3-hydroxy-1,4-dioxo-1,4-dihydronaphthalen-2-yl)benzoic acid, methyl-(3-methoxy-1,4-dioxo-1,4-dihydronaphthalen-2-yl)benzoic acid, methyl (3-methyl-1,4-dioxo-1,4-dihydronaphthalen-2-yl)benzoate 4-(3-hydroxy-5,5,8,8-tetramethyl-1,4-dioxo-1,4,5,6,7,8-hexahydroanthracen-2-yl)benzoic acid, methyl-4-(3-hydroxy-1,4-dioxo-1,4-dihydronaphthalen-2-yl-azo)benzoate, 4-(3-hydroxy-5,5,8,8-tetramethyl-1,4-dioxo-1,4,5,6,7,8-hexahydroanthracen-2-yl-azo)benzoic acid, 3-(3,5-di-tert-butyl-4-oxocyclohexa- 2,5-dienylidene)-5,5,8,8-tetramethyl-5,6,7,8-tetrahydrocyclopenta[b]naphthalen-1,2-dione, 3-(3,5-di-tert-butyl-4-oxocyclohexa-2,5-dienylidene)-5,5,8,8-tetramethyl-5,6,7,8-tetrahydroanthracen-3H-1,2,4-trione, 2-(3,5-di-tert-butyl-4-hydroxyphenyl)-3-methoxy-5,8-dimethyl-1,4-naphthoquinone, 2-(3,5-di-tert-butyl-4-hydroxyphenyl)-3-methoxy-6,7-dimethyl-1,4-naphthoquinone, 2-(3,5-di-tert-butyl-4-hydroxyphenyl)-3-methoxy-5-methyl-1,4-naphthoquinone, 2-(3,5-di-tert-butyl-4-hydroxyphenyl)-2-methoxy-5-methyl-1,4-naphthoquinone, 2-(3,5-di-tert-butyl-4-hydroxyphenyl)-3-methoxy-6-methyl-1,4-naphthoquinone; 3-(3,5-di-tert-butyl-4-hydroxyphenyl)-2-methoxy-6-methyl-1,4-naphthoquinone, 2-(3,5-di-tert-butyl-4-hydroxyphenyl)-3-methoxy-5,6-dimethyl-1,4-naphthoquinone, 3-(3,5-di-tert-butyl-4-hydroxyphenyl)-2-methoxy-6-methyl-1,4-naphthoquinone, 2-(3,5-di-tert-butyl-4-hydroxyphenyl)-3-methoxy-5,6-dimethyl-1,4-naphthoquinone, 3-(3,5-di-tert-butyl-4-hydroxyphenyl)-2-methoxy-5,6-dimethyl-1,4-naphthoquinone, 2-(3,5-di-tert-butyl-4-hydroxyphenyl)-3-methoxy-5,7-dimethyl-1,4-naphthoquinone, 3-(3,5-di-tert-butyl-4-hydroxyphenyl)-2-methoxy-5,7-dimethyl-1,4-naphthoquinone, 2-(3,5-di-tert-butyl-4-hydroxyphenyl)-3-ethylthio-5-methyl-1,4-naphthoquinone, 2-(3,5-di-tert-butyl-4-hydroxyphenyl)-3-ethylthio-6-methyl-1,4-naphthoquinone, 2-(3,5-di-tert-butyl-4-hydroxyphenyl)-3-hydroxy-5,8-dimethyl-1,4-naphthoquinone, 2-(3,5-di-tert-butyl-4-hydroxyphenyl)-3-hydroxy-6,7-dimethyl-1,4-naphthoquinone, 2-(3,5-di-tert-butyl-4-hydroxyphenyl)-3-hydroxy-5-methyl-1,4-naphthoquinone, 3-(3,5-di-tert-butyl-4-hydroxyphenyl)-2-hydroxy-5-methyl-1,4-naphthoquinone, 2-(3,5-di-tert-butyl-4-hydroxyphenyl)-3-hydroxy-6-methyl-1,4-naphthoquinone, 3-(3,5-di-tert-butyl-4-hydroxyphenyl)-2-hydroxy-6-methyl-1,4-naphthoquinone, 2-(3,5-di-tert-butyl-4-hydroxyphenyl)-3-hydroxy-5,6-dimethyl-1,4-naphthoquinone, 2-(3-brom-5-tert-butyl-4-hydroxyphenyl)-3-hydroxy-5,6-dimethyl-1,4-naphthoquinone, 3-(3,5-di-tert-butyl-4-hydroxyphenyl)-2-hydroxy-5,6-dimethyl-1,4-naphthoquinone, 2-(3,5-di-tert-butyl-4-hydroxyphenyl)-3-hydroxy-5,7-dimethyl-1,4-naphthoquinone, 3-(3,5-di-tert-butyl-4-hydroxyphenyl)-2-hydroxy-5,7-dimethyl-1,4-naphthoquinone.

Most especially preferred is Trolox (6-hydroxy-2,5,7,8-tetramethylchroman-2-carboxylic acid).

As described in the literature, the method according to the invention can be carried out at 4° C. to 90° C. The method is preferably carried out at a temperature between 35° C. and 70° C.

Suitable purification and depletion reactions are known to the person skilled in the art. For example, interfering reagents are depleted by ultrafiltration membranes, dialysis or absorption chromatography. It also possible, however, to dilute the treated DNA sample with water or with an aqueous solution so far that the reactants, especially bisulphite, do not interfere with the further reaction steps. It can also be beneficial to separate the treated DNA sample by precipitation and after washing add separately into the further processes in re-dissolved form.

Furthermore, suitable desulphonation reactions, especially those using suitable bases that are used during or subsequent to the purification and depletion reactions are known to the person skilled in the art.

The genomic DNA sample is preferably denatured thermally before treatment.

It can be beneficial to carry out step d) in two sub-stages as follows:
  d1) a PCR pre-amplification is carried out with at least one primer pair of different sequence which hybridise(s) non-specifically to a DNA sample pre-treated according to Claim 1 and thus produce(s) more than one amplificate in the PCR step;
  d2) a PCR amplification of the product formed in the pre-amplification is carried out with primers of different sequence which are each time identical or reversely complementary to a segment of the DNA sample [(+)-strand or (−)-strand] pre-treated according to Claim 1 and which specifically hybridise to the DNA to be amplified.

It can also be beneficial that the amplification of several DNA segments are carried out in one reaction vessel.

It is preferable that a heat-stable DNA polymerase is used for the polymerase reaction.

It is especially preferred that a desulphonation of the DNA is carried out prior to step d) according to the method of the invention. However, it can also be beneficial to carry out the desulphonation of the DNA during steps d) or e).

It is also preferred that for the detection of the pre-treated DNA the PCR products are hybridised on an oligonucleotide array and the following sub-steps are then carried out:
  a) the amplified genomic DNA is hybridised to at least one oligonucleotide with the formation of a duplex, wherein said hybridised oligonucleotides adjoin directly with their 3'-ends or at a separation of up to 10 bases to the positions which are to be investigated in respect of their methylation in the genomic DNA sample;
  (b) the oligonucleotide with known sequence of n nucleotides is extended by at least one nucleotide by means of the polymerase, wherein the nucleotide carries a detectable tag and the extension is dependent upon the methylation status of the respective cytosine in the genomic DNA sample.

It is preferred that for the detection of the pre-treated DNA, the PCR products are hybridised on an oligonucleotide array and then the following sub-steps are carried out:
- (a) a set of oligonucleotides is hybridised to the amplified genomic DNA with the formation of a duplex, wherein this set of oligonucleotides is comprised of two different species and wherein the hybridised oligonucleotides of the first species adjoin directly with its 3'-end or at a separation of up to 10 bases to the positions that are to be investigated in respect of their methylation in the genomic DNA sample and wherein the second oligonucleotide of the second species is hybridised to a second region of the target molecule so that the 5'-end of the oligonucleotide of the second species is separated by a gap of the size of a single nucleotide or up to 10 nucleotides from the 3'-end of the hybridised oligonucleotide of the first species at the site of the said selected position;
- (b) the oligonucleotide of the first species with known sequence of n nucleotides is extended by means of a polymerase by at most by the number of nucleotides that lie between the 3'-end of the oligonucleotide of the first species and the 5'-end of the oligonucleotides of the second species, wherein the extension is dependent upon the methylation status of the respective cytosine in the genomic DNAS species;
- (c) The oligonucleotides are incubated in the presence of a ligase, wherein the adjoining oligonucleotide of the first species extended in the polymerase reaction and the oligonucleotide of the second species are connected and in that way a ligation product is obtained, provided that in the previous stage an extension of the oligonucleotide of the first species takes place in such a manner that the 3'-end with available 3'-hydroxy function of the extended oligonucleotide now directly adjoins the 5'-end of the oligonucleotide of the second species.

It is especially preferred thereby that oligonucleotide of the first species used and/or the oligonucleotide of the second species used comprise either only the bases T, A and C or the bases T, A and G.

It is also preferred that for detection of the pretreated the PCR products are hybridised on an oligonucleotide array and then the following sub-steps are carried out:
- (a) The amplified genomic DNA is hybridised to at least one oligonucleotide with known sequence of n nucleotides with the formation of a duplex, wherein said hybridised oligonucleotides with their 3'-end hybridise partially or completely to the positions that are to be investigated in respect of their methylation in the genomic DNA sample;
- (b) the oligonucleotide, provided that beforehand it hybridised with its 3'-terminus to the position under investigation without base mispairings, is extended by at least one nucleotide by means of a polymerase, wherein at least one nucleotide bears a detectable tag and the extension is dependent upon the methylation status of the respective cytosine in the genomic DNA sample.

It is also preferred that the PCR products and/or extension products and/or ligation product are provided with a detectable tag for detection.

In particular it is thereby preferred that the tags are fluorescent tags and/or the tags are radionuclides. It is particularly preferred thereby that the tags of the nucleotides are detachable mass tags that can be detected in a mass spectrometer.

It is also especially preferred that the PCR products and/or extension products and/or ligation products are detected as a whole in the mass spectrometer and are thus unambiguously characterised by their mass. It is also preferred according to the invention that in each case a fragment of the PCR products and/or extension products and/or ligation products is each time detected in the mass spectrometer.

The method according to the invention is also preferably characterised in that the fragment of the PCR product and/or extension product and/or ligation product is produced by digestion with one or more exo- or endonucleases.

It is further preferred that for improved detectability in the mass spectrometer the fragments produced are provided with a single positive or negative net charge.

It is most particularly preferred that the PCR products and/or the extension products and/or the ligation products are detected and visualised by matrix-assisted laser desorption/ionisation mass spectrometry (MALDI-TOF) or by electrospray mass spectrometry (ESI).

The method according to the invention is suitable both for DNA from extracellular sources and also from DNA from cells.

The method according to the invention is especially suited for applications in which the genomic DNA is obtained from a complex DNA source, wherein said source comprises in particular cell lines, seminal fluid, vaginal fluid, lung and bronchial lavage, blood, sputum, stool, urine, cerebrospinal fluid and other body fluids that can contain freeflow extracellular DNA, non-imbedded or imbedded tissue, for example imbedded or non-imbedded tissue from eyes, intestine, kidney, brain, heart, prostate, lung, breast, liver or other organs or musculature, histological microscopic slides and all possible combinations thereof.

A further subject matter of the present invention is the use of a method according to the invention for diagnosis and/or prognosis of adverse events for patients or individuals, wherein these adverse events belong to at least one of the following categories: undesired drug effects; cancer; CNS disorders, damage or disease symptoms of aggression or behavioural disorders; clinical, psychological and social consequences of brain damage, psychotic disorders and personality disorders, dementia and/or associated syndromes; cardiovascular disease, dysfunction and damage; dysfunction, damage or disease of the gastrointestinal tract; dysfunction, damage or disease of the respiratory system; injury, inflammation, infection, immunity and/or recovery; dysfunction, damage or disease of the body as aberration in the developments process; disorder, damage or disease of the skin, muscle, connective tissue or bone; endocrine or metabolic dysfunction, damage or disease; headaches or sexual dysfunction.

Subject matter of the invention is also the use of a method of the invention for distinguishing cell types or tissues or for the investigation of cell differentiation.

A further subject matter of the present invention is finally a kit comprising at least one reagent comprising a bisulphite, tetrahydrofurfuryl alcohol (optionally denaturating reagents and/or solvents) as well as radical scavengers and optionally primers for the preparation of amplificates as well as directions for undertaking an assay according to the method of the invention.

The present invention provides a automatable method for the detection of methylcytosine that comprises only pipetting stages. In this way the efficiency of existing methods is improved in respect of simplicity of handling, quality, cost and most beneficially throughput.

The invention claimed is:

1. Method for the detection of cytosine methylations in DNA, comprising:
   a) incubating a genomic DNA sample with a solution of a bisulphite in a concentration range from 0.1 to 6 mol/l, wherein tetrahydrofurfuryl alcohol is present;
   b) the reaction mixture obtained is either subjected to purification or depletion so that a reagent added in a) are is removed, or the DNA sample is diluted with water or an aqueous solution so that a reagent added in a) does not interfere with a subsequent reaction;
   e) conducting a detection as to what extent a sequence has changed in comparison with the genomic DNA sample prior to said incubating, and a conclusion is made on the methylation status of at least one locus in the genomic DNA sample.

2. Method according to claim 1, wherein said solution comprises at least one radical scavenger.

3. Method according to claim 1, wherein the DNA sample is subjected to desulphonation either during purification or depletion, or the DNA sample is subjected to desulphonation in a subsequent reaction.

4. Method according to claim 1 wherein the DNA sample is amplified in a polymerase reaction prior to said detection.

5. Kit adapted for carrying out a method according to claim 1, wherein the kit comprises at least one reagent comprising bisulphite and tetrahydrofurfuryl alcohol.

6. Kit according to claim 5, wherein the kit further comprises at least one radical scavenger.

7. A method of claim 4, wherein said solution further comprises at least one radical scavenger.

8. A method of claim 1, wherein said solution further comprises at least one denaturing solvent and/or reagent.

9. A method of claim 7, further comprising at least one denaturing solvent and/or reagent.

10. Method according to claim 3, wherein said solution comprises at least one radical scavenger.

11. Method according to claim 8, wherein said solution comprises at least one radical scavenger.

12. A kit of claim 5, further comprising at least one denaturing solvent and/or reagent.

13. A kit of claim 6, further comprising at least one denaturing solvent and/or reagent.

14. Kit adapted for carrying out a method according to claim 3, wherein the kit comprises at least one reagent comprising bisulphite and tetrahydrofurfuryl alcohol.

15. Kit adapted for carrying out a method according to claim 4, wherein the kit comprises at least one reagent comprising bisulphite and tetrahydrofurfuryl alcohol.

16. The method of claim 1, wherein the method is carried out at a temperature from 4° C. to 90° C.

17. The method of claim 1, wherein the method is carried out at a temperature from 35° C. to 70° C.

18. The method of claim 1, wherein the genomic DNA sample is denatured thermally before treatment.

19. The method of claim 2, wherein the radical scavenger is 6-hydroxy-2,5,7,8-tetramethylchroman-2-carboxylic acid.

20. The kit of claim 6, wherein the radical scavenger is 6-hydroxy-2,5,7,8-tetramethylchroman-2-carboxylic acid.

* * * * *